United States Patent [19]

Gough et al.

[11] Patent Number: 4,703,756

[45] Date of Patent: Nov. 3, 1987

[54] COMPLETE GLUCOSE MONITORING SYSTEM WITH AN IMPLANTABLE, TELEMETERED SENSOR MODULE

[75] Inventors: David A. Gough, Cardiff; Joseph Y. Lucisano; Jon C. Armour, both of La Jolla; Brian D. McKean, San Diego, all of Calif.

[73] Assignee: The Regents of the University of California, Berkeley, Calif.

[21] Appl. No.: 860,184

[22] Filed: May 6, 1986

[51] Int. Cl.[4] ............................................. A61B 5/00
[52] U.S. Cl. .................................... 123/635; 204/403; 204/415
[58] Field of Search ................ 128/635; 204/403, 415, 204/431

[56] References Cited

U.S. PATENT DOCUMENTS

| | | | |
|---|---|---|---|
| 3,542,662 | 11/1970 | Hicks et al. | 204/195 |
| 3,957,613 | 5/1976 | Macur | 128/635 |
| 4,240,438 | 12/1980 | Updike et al. | 204/403 X |
| 4,340,457 | 7/1982 | Kater | 204/403 X |
| 4,361,153 | 11/1982 | Slocum et al. | 128/419 P |
| 4,366,033 | 12/1982 | Richter | 128/635 X |
| 4,431,004 | 2/1984 | Bessman et al. | 128/635 |
| 4,458,686 | 7/1984 | Clark, Jr. | 128/635 |
| 4,484,987 | 11/1984 | Grough | 204/403 X |
| 4,494,950 | 1/1985 | Fischell | 128/635 |
| 4,541,431 | 9/1985 | Ibrahim et al. | 128/419 |
| 4,550,732 | 11/1985 | Batty, Jr. et al. | 128/419 |
| 4,553,547 | 11/1985 | Keimel | 128/419 |
| 4,571,589 | 11/1982 | Slocum et al. | 128/419 P |

OTHER PUBLICATIONS

Conway et al, "Radio Telemetry . . . in vivo", Biomed Eng., Oct. 1973, vol. 8, No. 10, pp. 428–430.
"A Membrane Combination for Implantable Glucose Sensor Measurements in Undiluted Biological Fluids", by U. Fischer & P. Abel, vol. XXVIII, Trans. Am. Soc. Artif. Intern. Organs, 1982, pp. 245–248.

Primary Examiner—Lee S. Cohen
Attorney, Agent, or Firm—Brown, Martin Haller & Meador

[57] ABSTRACT

An electrochemical system includes a sensor module suitable for implantation in the body to monitor glucose and oxygen levels therein. The module has two oxygen sensors situated in an oxygen-permeable housing, arranged in a tandem relationship, and recessed in the housing, one sensor being unaltered and the other contacting glucose oxidase allowing for differential measurement of oxygen content in bodily fluids or tissues indicative of glucose levels. The module includes a communication capability for transmitting measurement information to an external recording device outside the body.

23 Claims, 8 Drawing Figures

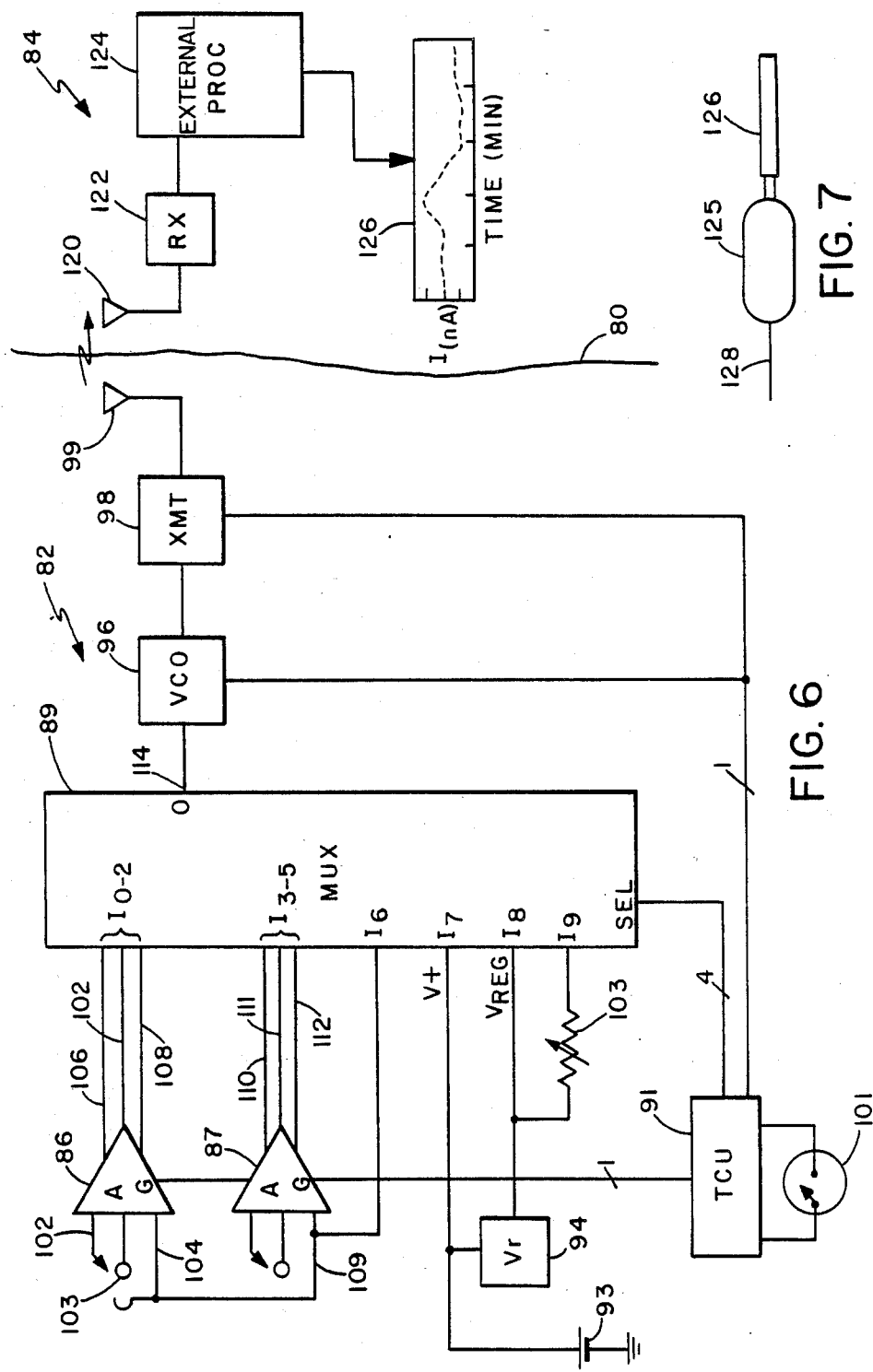

4,703,756

COMPLETE GLUCOSE MONITORING SYSTEM WITH AN IMPLANTABLE, TELEMETERED SENSOR MODULE

STATEMENT OF GOVERNMENT INTEREST

This invention was made with Government support under Grant No. 5RO1AM27541 awarded by the National Institutes of Health. The Government has certain rights in this invention.

BACKGROUND OF THE INVENTION

This invention relates to glucose monitoring by means of an implantable sensor module having a transcutaneous telemetering ability.

Diabetes mellitus is treated with injections of insulin in order to counter the inability of the pancreas to manufacture and secrete insulin in response to elevated glucose levels. For this treatment to be effective, it is necessary to be able to monitor the glucose concentration in the body so as to specify the appropriate amount and time of administration of insulin. This requires a device for measuring glucose levels in the body. Thus, considerable research has been expended to develop an effective implantable glucose sensor.

A considerable number of implantable glucose sensors are premised on the so-called "enzyme electrode." The enzyme electrode consists of an immobilized enzyme that catalyzes a chemical reaction involving glucose and oxygen which can be readily monitored. Generally, the enzymatic reaction involves the catalytic conversion of glucose to gluconic acid with simultaneous consumption of oxygen. The enzyme responsible for this action is glucose oxidase. The decrease in oxygen is measured by an amperometric oxygen electrode.

Several implantable glucose sensors are presently available. For example, Bessman et al. in U.S. Pat. No. 4,431,004 describes a method and apparatus for determining glucose content by sensing the absolute level of oxygen concentration in the blood, and correcting the output differential measurement indicative of the glucose content according to the absolute level of oxygen. In addition, the Bessman et al. device compensates for temperature fluctuations in the body by having a thermistor included in the electrosystem. U.S. Pat. No. 4,458,686 of Clark describes a subcutaneous method of measuring glucose in bodily fluids. Glucose oxidase is injected beneath the dermis where it reacts with glucose, and in the process consumes oxygen. The resulting decrease in oxygen is sensed by a transcutaneous electrode placed over or near the injection site. The byproducts of the catalytic reaction, gluconic acid and hydrogen peroxide diffuse away from the site, and then are removed by the blood stream.

In addition to the implantable glucose sensors mentioned above, there also exist several devices that are suitable for detecting glucose in vitro, but have severe limitations when used in vivo. For example, Hicks et al. U.S. Pat. No. 3,542,662 describes a dual electrode system having an enzyme-containing membrane disposed between a fluid bead assay and a first oxygen sensor electrode, and a similar membrane not containing enzymes disposed between a fluid and second reference electrode. Oxygen diffuses through the enzyme-containing membrane and is consumed in an equal molar reaction with glucose catalyzed by glucose oxidase. Consequently, oxygen is unavailable for detection by the oxygen sensor electrode. The second oxygen sensor electrode measures the concentration of oxygen existing in the absence of the enzyme-catalyzed reaction. Thus, the difference in oxygen levels detected by the two electrodes is proportional to the glucose concentration. While this sensor works adequately in vitro, in vivo the device is unreliable in that it does not function adequately in low-oxygen environments.

At present there does not exist an implantable glucose sensor suitable for detecting glucose in regions of the body where oxygen concentrations are lower than glucose concentrations. However, Fisher and Abel in "A Membrane Combination for Implantable Glucose Sensors, Measurements in Undiluted Biological Fluids" (*Trans. Am. Soc. Artif. Intern. Organs,* Volume XXVIII, 1982), have approached the problem by fabricating an oxygen electrode sensor that has disposed about its working face a hydrophobic layer in contact with an enzyme layer. The hydrophobic layer has a minute hole that is aligned with the oxygen electrode sensor beneath it so as to allow predominantly access of glucose to contact the enzyme layer directly above the oxygen electrode. The hydrophobic layer is composed of material that is predominantly permeable to oxygen, and not glucose. Thus, oxygen diffuses into the enzyme layer at all points across the surface of the hydrophobic layer whereas glucose diffuses in only through the hole in the hydrophobic layer. While this design effectively establishes a stoichiometric excess of oxygen over glucose in a region of the enzyme layer, it has several unattractive features. First the small amount of enzyme disposed for action on glucose entering the minute hole tends to become inactivated in a relatively short time. Moreover, because glucose entry is restricted to a hole in the hydrophobic membrane, the range of glucose concentrations detectable is narrow.

An additional desirable feature of a glucose monitoring system that is not presently available is a telemetry capability that would transcutaneously transmit data relevant to the glucose levels present in the body to an apparatus outside the body capable of continuously monitoring the user's status.

Transcutaneous telemetry systems having implantable electrode modules are known in the art. For example, there are pacemakers available which, when implanted and connected to the heart, can monitor electrocardial activity through electrodes attached to the pacemakers. The electrodes function as electropotential sensors, and the pacemakers include interface circuitry which buffers the sensor signals, formats them, and transmits the formatted signals by way of a bi-directional RF communication link to an external communication module. The telemetered signals are monitored and processed through the external module.

Further, it is known in the art to provide for enablement of two or more functions within implanted devices. For example, the implantable pacemakers can be programmed to switch electrode functions from passive electrocardial monitoring to active electrical stimulation. The switching of function can be implemented by means of a command transmitted to the implanted device from the external module via the RF link. Programmable circuitry in the implanted device alters electrode function in response to the commands. In this regard, see U.S. Pat. No. 4,550,732 of Batty, Jr. et al. and U.S. Pat. No. 4,571,589 of Slocum et al.

However, at present, there are no systems that include the means to transcutaneously monitor physiochemical processes in the body. Such systems would be very useful in the glucose-monitoring example given above.

SUMMARY OF THE INVENTION

An implantable electrochemical glucose monitoring system is described that functions in tissues or fluids of the body with different oxygen concentrations and which permits measuring glucose over a range of concentrations therein. The system utilizes two oxygen sensors situated in a tandem relationship within a housing. The first oxygen sensor is unaltered and is positioned behind the second oxygen sensor. The second oxygen sensor contacts glucose oxidase which is impregnated in a membrane and disposed about the sensor. Both oxygen sensors are recessed in the housing and communicate with bodily fluids wherein they measure an oxygen content differential in the bodily fluids. The housing is connected to electronic circuitry, linked by a communication channel to an external unit outside the body. The differential oxygen measurement is amplified and then transmitted by the circuitry to the external unit.

BRIEF DESCRIPTION OF THE DRAWINGS

References are made herein below to the drawings, which illustrate various embodiments of the invention and, in which:

FIG. 6 is a block diagram illustrating the electronics interface of the invention.

FIG. 7 is an illustration of assembled internal electronics connected to a catheter containing oxygen sensors.

DETAILED DESCRIPTION OF THE INVENTION

It is important to note that while the present invention will be described as applied to determining concentrations of glucose in bodily fluids, particularly fluids containing a large stoichiometric excess of glucose over oxygen, that the monitoring system described herein is not limited to ascertaining glucose and oxygen. Indeed, it will be easily understood by those skilled in the art that it is readily applicable to detect other molecules such as amino acid, lactate, ammonia, or the like commonly found in bodily fluids that are substrates for oxidase enzymes and that require the presence of a gaseous species to undergo enzymatic conversion. It is also appreciated that the system may be readily applied to monitoring substances in bioreactor vessels or similar environments.

Figure 1:
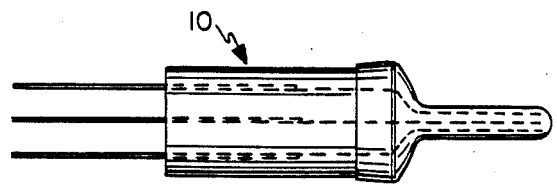
FIG. 1 is an illustration of an oxygen sensor.
Figure 2:
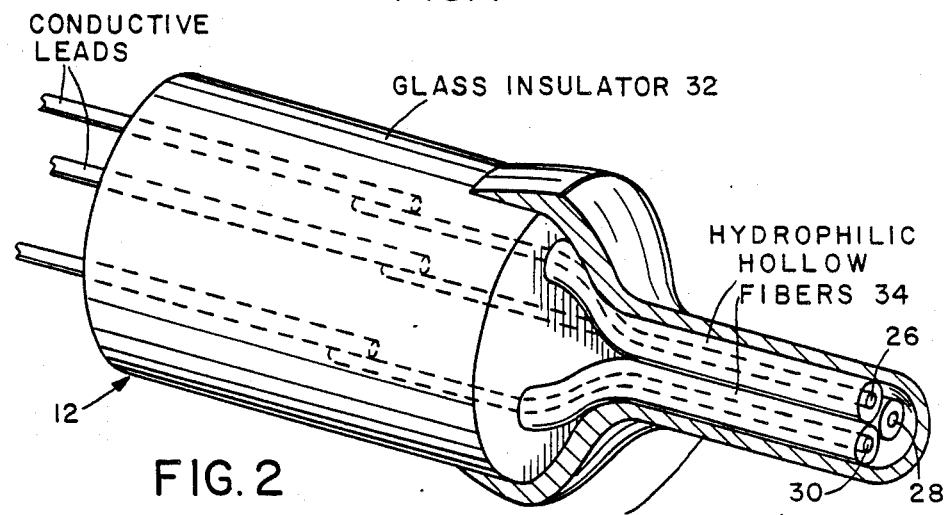
FIG. 2 is an enlarged presentation of the oxygen sensor shown in FIG. 1.
Figure 3:
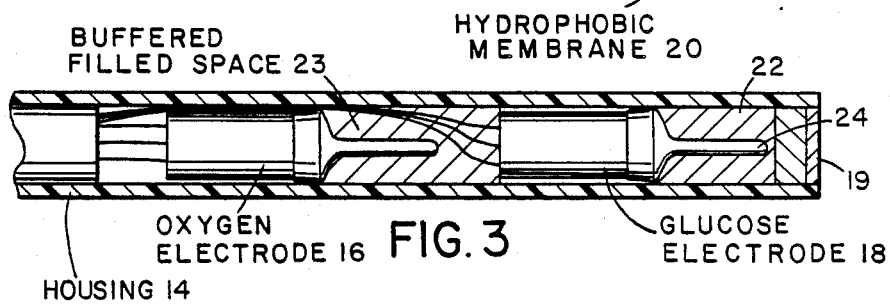
FIG. 3 depicts first and second oxygen sensors situated in a catheter.

A glucose monitor suitable for implantation will now be described with reference to the figures. It consists of a housing, having situated therein two oxygen sensors. FIGS. 1 and 2 depict the oxygen sensors, 10, 12, while FIG. 3 shows a pair of oxygen sensors 16 and 18 situated in a housing 14. A catheter is the preferred housing, as it allows facile impantation of the device. Moreover, a catheter made of material that is permeable to oxygen and relatively impermeable to glucose is desirable. Since the conversion of glucose to gluconic acid is limited by whichever chemical, glucose or oxygen, is present in lowest concentration, in order to have the device function adequately over a wide range of glucose concentrations, oxygen must be at least stoichiometrically equal to glucose in the enzyme region. Thus, by having a catheter which hinders the rate of entry of glucose, but permits access of oxygen to the interior of the catheter, an effective means of varying the concentration of oxygen relative to that of glucose is provided.

Figure 4:
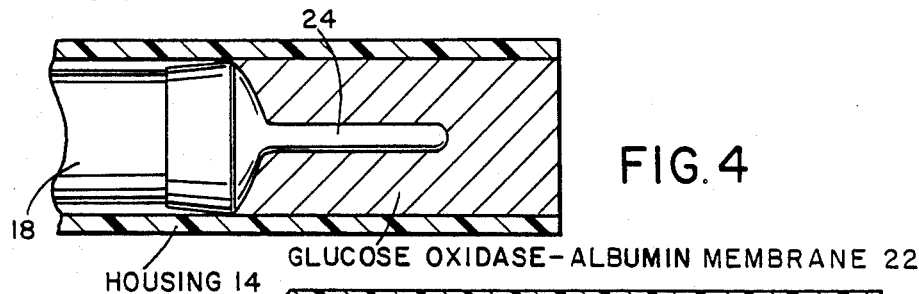
FIG. 4 schematically represents the second oxygen sensor situated in the catheter and recessed from the tip thereof, and reveals the presence of a glucose oxidase-membrane surrounding the electrode sensing region of the sensor.

The two oxygen sensors 16 and 18 situated in the housing 14 shown in FIG. 3 exhibit a tandem relation, and both of the sensors are recessed from the tip 19 of the catheter. The first oxygen sensor 16 is unaltered and is situated behind the second oxygen sensor 18. The first oxygen sensor 16 measures ambient oxygen, while the second sensor 18 measures a lower level of oxygen arising from the consumption of oxygen in the oxidation of glucose in the enzymatic reaction described infra. FIG. 4 reveals that in order to realize a decrease in oxygen brought about by the oxidation of glucose, the oxygen sensor used to detect glucose dependent oxygen levels, for example 18, has disposed about its working regions a gelstionous layer 22 or membrane made of hydrophilic material. This layer contacts the working electrode area of the oxygen sensor. Contained within, or associated with the gelatinous material 22 is an enzyme, glucose oxidase, and optionally a second enzyme, catalase. The latter enzyme is useful to decompose hydrogen peroxide generated in the oxidation of glucose. Catalase catalyzes the following reaction:

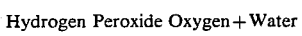

Hydrogen Peroxide Oxygen+Water

The sensor that measures oxygen independent of glucose concentrations can have a similar membrane disposed about its working region but lacking glucose oxidase or catalase. Such a membrane can act as a buffer, filling the space 23 between the sensors 16 and 18 in FIG. 3.

Materials useful for preparing the gelatinous layer 22 include polyacrylamide gels, glutaraldehyde-cross-linked proteins, particularly collagen or albumin, polyhydroxyethyl-methacrylate, and its derivatives, and other hydrophilic polymers and copolymers. The layer can also be constructed of cross-linked glucose oxidase, or other enzymes with chemical cross-linking reagents. The materials and methods used for preparing the gelatinous layer are described in U.S. Pat. No. 4,484,987, which is incorporated herein by reference.

It is important to note that the sensitivity and response time of the implantable monitoring system can be altered simply by varying the amount of electrode surface area of the second oxygen sensor, as well as the thickness of the hydrophilic membrane 22 surrounding the sensor working region. Additionally, as FIG. 4 shows the membrane 22 containing glucose oxidase can be disposed in front of, as well as around, a hydrophobic layer 24 which allows the user to optimize the sensitivity and response time of the system depending on the oxygen and glucose environments in which it is implanted.

FIG. 2 shows that the oxygen sensors 12 exhibits a three electrode design having a working electrode 26, a counter electrode 28, and a reference electrode 30. The working and counter electrodes 26 and 28, respectively, are generally fabricated from a noble metal, while the reference electrode 30 can be a standard silver/silver chloride electrode. The electrode assembly is mounted in electrically insulating material 32, such as glass, epoxy or the like, but leaving an exposed working face. The exposed regions of the three electrodes are positioned so as to prevent direct physical contact with each other; in addition, they may be sheathed. Hollow fibers 34 are suitable for optional sheating of the electrodes. Alternatively, the electrode assembly is coated with a hydrated gel or the like, particularly, poly(2-hydroxyethylmethacrylate) so as to provide an aqueous environment for electrolytic communication. Lastly, the electrode assembly may be coated with a hydrophobic polymer to inhibit access of polar solutes to the electrode.

As with the sensor 12, the second oxygen sensor 18 of FIG. 4, exhibits a hydrophobic membrane 22 that is permeable to oxygen but relatively impermeable to glucose. Further in addition to containing glucose oxidase, the membrane has similar permeability properties as that described for the catheter 14. That is, it retards the rate of glucose but not oxygen entry to the working region of the sensor electrodes. This effectively raises the oxygen concentration relative to glucose concentation ensuring adequate enzymatic substrates. Also, as taught to above, depending on the relative concentrations of oxygen and glucose that the monitoring system is implanted into, the first oxygen sensor, 16 of FIG. 3, may, or may not have a hydrophobic membrane about the three electrode assembly. The reason for having the hydrophobic membrane about the first electrode in some instances is that, in addition to effectively increasing the oxygen concentration accessible to the electrodes, it also acts as a barrier to contaminants which can disrupt oxygen detection at either the first or second sensors.

The hydrophobic membrane 24 associated with the second sensor 18 of FIG. 3 and perhaps the first sensor 16, is made up of oxygen permeable material such as polydimethylsiloxane, polymers of tetrafluoroethylene or its fluor-chloro analogs alone or as copolymers with ethylene or propylene, polyethylene, polypropylene, cellulose acetate, and other oxygen-abiding polymeric materials. The method of making the membrane as well as its physical properties are described in U.S. Pat. No. 4,484,987.

The three electrode assemblies of either the first and second oxygen sensors communicate with implanted telemetry electronics by lead wires that are attached to the electrodes.

Figure 5:
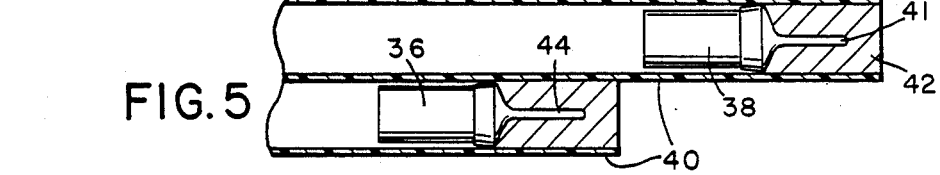
FIG. 5 shows a second embodiment wherein the first and second oxygen sensors are situated in a bilumen catheter.

A second embodiment of the subject invention is shown in FIG. 5. The sensor design shown in FIG. 2, and the other materials described above, are favorably employed here. However, the first 36 and second 38 oxygen sensors are situated in a bilumen catheter 40 in lieu of a single lumen catheter. In this embodiment, the first 36 and second 38 oxygen sensors occupy a substantially parallel spaced relationship to one another. Both oxygen sensors are recessed in the catheter. Disposed about the active sensing region of the second oxygen sensor, 38 and in communication with the hydrophilic layer 41 about the three electrode assembly, is a hydrophilic membrane containing glucose oxidase as described above. The first oxygen sensor 36 as described above for the single lumen catheter may or may not exhibit a hydrophobic membrane about the three electrode assembly. If the bilumen catheter 40 is implanted in a region of the body where it is likely to encounter cellular debris, or the presence of substances that interfere with the detection of oxygen, the hydrophobic membrane 44 may be favorably disposed about the first oxygen sensor in as much as it will effectively retard the substances from contacting the electrode assembly of the sensor.

Electronic processing and telemetering is employed in connection with the above-described sensors, which is useful for buffering the electrical signals developed by the sensors, processing the sensor signals for transmission, and communicating the buffered, processed signals via a telemetry link to an external monitoring unit. The electronics necessary for the buffering, processing, and telemetering functions is illustrated in FIG. 6. In FIG. 6 the cutaneous barrier separating the interior and exterior of a body is illustrated by reference numeral 80. A set of internal electronics 82 are shown to the left of the skin barrier 80. It is understood that the internal electronics are contained in a module implanted under the skin of a body. It is further understood that the internal electronics are connected to a catheter containing oxygen sensors described above. To the right of the barrier 80, outside the body in which the internal electronics 82 are implanted, is an external unit 84. The telemetry link comprises the internal electronics in combination with the external antenna 120 and receiver (RX) 122.

With regard to the electronics 82, which are implanted in a body for oxygen and glucose monitoring, it will be understood that the actual physical implementation of the electronic functions to be described can be realized through well-known techniques of hybridization and miniaturization. Therefore, it is to be understood that the internal electronics 82 can be manufactured in a miniature size suitable for being received in a module described below, for being implanted in a body. The internal electronics 82 include a pair of potentiostat amplifiers (A) 86 and 87 which are useful for maintaining a set potential between a pair of electrodes and measuring a current generated by one of the electrode pairs after setting the potential. The internal electronics further include an analog multiplexer (MUX) 89, a timing and control unit (TCU) 91, a battery 93, a high-quality voltage regulator ($V_r$) 94, a voltage-controlled oscillator (VCO) 96, an RF transmitter (XMT) 98, and an antenna 99. Associated with the TCU 91 is a magnetically-controlled, reed switch 101 which selects one of three operating modes of the implanted electronics 82.

Potentiostat amplifiers such as 86 and 87 are well-known in the art, and a description of one will suffice for a description of both. Therefore, with respect to the potentiostat amplifier 86, three input leads, each connected to an electrode, are provided, and are indicated by 102, 103, and 104, respectively. The input lead 102 is connected to a working electrode attached to a sensor as described hereinabove. The lead 103 attaches to a reference electrode, while the lead 104 attaches to a counter electrode. As is known, the working electrode provides a current having an amplitude corresponding to the chemical process catalyzed by the sensor attached to it. The reference electrode provides a calibrated reference voltage for operation of the amplifier 86, while the counter electrode provides a return path, corresponding essentially to the ground lead for the amplifier 86. As is known, the amplifier 86 can provide up to three signals, each being provided on a respective one of the output signal leads 106, 107, and 108. The amplifying action of the amplifier 86 is essentially that of a current-to-voltage amplifier, the operation of which is well-understood in the art. The amplifying action converts the signal current from the working electrode on lead 102 into an amplified voltage value. This value is provided on the signal lead 106. In addition, the potentiostat amplifier 86 has the capability of providing the reference voltage on signal line 103 that is produced by the reference electrode. This voltage value is provided on the signal line 107. Finally, the amplifier 86 has the capability of providing, on signal output lead 108, the differential voltage measured between signal lines 102 and 103. The amplifier 86 also has a two-state gain characteristic. In this regard, the amplification gain employed in the conversion of the working electrode current to the voltage on signal line 106 can assume one of two values, depending upon the signal input to the gain select (G) port of the amplifier 86. This signal is provided as a control output signal from the TCU 91. In the preferred embodiment, the second gain characteristic of the amplifier 86 is ten times the value of the first gain characteristic. Thus, when the signal on the gain select port of the amplifier is switched from the low to the high value, the amplitude on the signal line 106 increases by a factor of 10.

For clarity in the discussion which follows, the amplified voltage on signal line 106 is denoted as VA (for "amplified voltage"), the voltage on signal line 107 is denoted as Vref, while the signal on signal line 108 has the mnemonic $V_W$.

The potentiostat amplifier 87 is identical to the amplifier 86, with the exception that the working and reference leads are connected to electrodes that are distinct from the electrodes connected to the corresponding leads of the amplifier 86. However, the amplifier 87 is also connected to the counter electrode that is coupled to the amplifier 86. In the preferred embodiment, the working electrodes connected to the amplifiers 86 and 87 are differentiated as described above. In this regard, for example, the working electrode of the amplifier 86 can consist of a non-catalyzed oxygen sensor of the type described above, while the working electrode of the amplifier 87 can consist of an enzyme-containing oxygen sensor of the type described above. As is known, the process being monitored can be quantified by processing the difference in the currents generated by the working electrodes. Therefore, the principal function of the internal electronics 82 is to transform the working electrode currents into signals that are suitable for transmission through the skin barrier 80 to the external unit 84. The external unit 84 measures the difference, and provides a visible indication of the measurement.

To complete the description of the amplification functions of the amplifier 87, an amplified voltage signal, representing the current on the working electrode attached to the amplifier 87 is provided on signal lead 110, the reference voltage value on signal lead 111, and the differential voltage measured between the working and reference electrodes is output on signal lead 112.

The output signal leads from the amplifiers 86 and 87 are connected to the MUX 89, which consists of a conventional analog multiplexer having a plurality of input ports I0–I9, an input selection port array (SEL), and an output port O. The output port is connected to output signal lead 114. Selection of an input port to be connected to the output port O is conventionally determined by the signal provided to the SEL port of the MUX 89.

The TCU 91 is composed of conventional digital timing and control circuitry and has the principal functions of determining the gain of the amplifiers 86 and 87, and the selection of an input port. The TCU 91 can consist of, for example, a conventional programmed logic array (PLA) or other programmable circuit programmed to cycle through a predetermined state sequence that will cause all possible combinations of amplifier gains and input port selections to be effected during completion of a major cycle. In addition, the TCU 91 is configured to run in two or more modes in response to signals from the magnetic reed switch 101. The magnetic reed switch 101 is conventional and consists of a magnetically-actuated switch implanted in close proximity to the skin barrier 80, where its contact configuration is set by the influence of a magnet brought into close proximity with the switch, the magnetic field extending through the skin barrier 80 to effect switch-setting. Such an arrangement is conventional, and reference is given to U.S. Pat. No. 4,361,153 for an understanding of it.

Also input to the MUX 89 is the positive electrode (denoted as $V_+$) of the battery 93, and the output port ($V_{reg}$) of the high-precision voltage regulator 94. A conventional thermistor 103 is connected to an input port of the MUX 89 to provide an indication of internal body temperature. Finally, connection is also provided between the counter electrode and the MUX 89.

The output signal lead 114 of the MUX 89 is fed to the VCO 96, whose output is, in turn, connected to the transmitter 98. As is conventional, the voltage present at the output port, conducted to the VCO 96 on signal lead 114, determines the frequency of oscillation of the VCO 96. The adjustable frequency of the VCO 96 is used to modulate an RF carrier output by the transmitter 98, which is broadcast through the skin barrier 80 by the antenna 99. The RF transmitter and VCO are gated on by a control output from the TCU 91 in order to reduce the power consumed by the internal electronics 82.

The external unit electronics 84 consist of a pick-up antenna 120 connected to an RF receiver (RX) 122, which detects and demodulates the carrier transmitted by the transmitter 98 included in the implanted module. The demodulated signal produced by the RX 122 is fed to an external processor 124 which converts the demodulated signal into an output signal suitable for driving an output graphics device. For example, the output graphics device can comprise a recorder 126 configured for recording the variations in amplitude of a current (I) over time.

A schematic of the physical management of the implantable portion of the electrochemical system of the invention is illustrated in FIG. 7. The internal electronics 82 are sealed in a biocompatible resin which is impermeable to moisture and formed into a smooth module 125 having a rounded profile to facilitate its use as an implant. Leads are brought out of the module which allow connection to a sensor catheter 126 and to the antenna 128. The lithium cell is contained in the electronics module.

The communications scheme can conventionally be converted to allow an infrared, or passive RF link. As is known, these are typically short range systems. However, an infrared link would theoretically allow a much higher data bandwidth than is possible with a passive RF link. A conventional passive link can involve an inductive communications scheme based upon creation of a strong magnetic field modulated by the transmitter 98. It will be evident to those skilled in the art that such a passive RF scheme will require appropriate shielding for the electronics 82 as well as shielding and filtering for the electrodes leads.

Typically, electrolyte penetration of the moisture barriers surrounding the leads extending between sensors and amplifiers can cause leakage paths for electrical signals between the leads. A particularly debilitating situation occurs when such a leakage path shunts the current from one electrode lead to another. Since very low current levels are being conducted, any error can be significant. Another undesirable effect would be the conduction of current between the reference and either the working or counter electrodes. In order to detect such problems so that appropriate actions can be taken to either replace sensors, electronics, or batteries, the system of the invention provides for monitoring more signals than just the transformed, amplified working electrode signal. By providing additional monitoring of the reference voltage amplitude, the amplitude of the differential voltage between the working and reference electrodes, and the battery, the system of the invention permits early detection of problems characteristically encountered in the implantation of electronic sensors in the human body.

Figure 8:
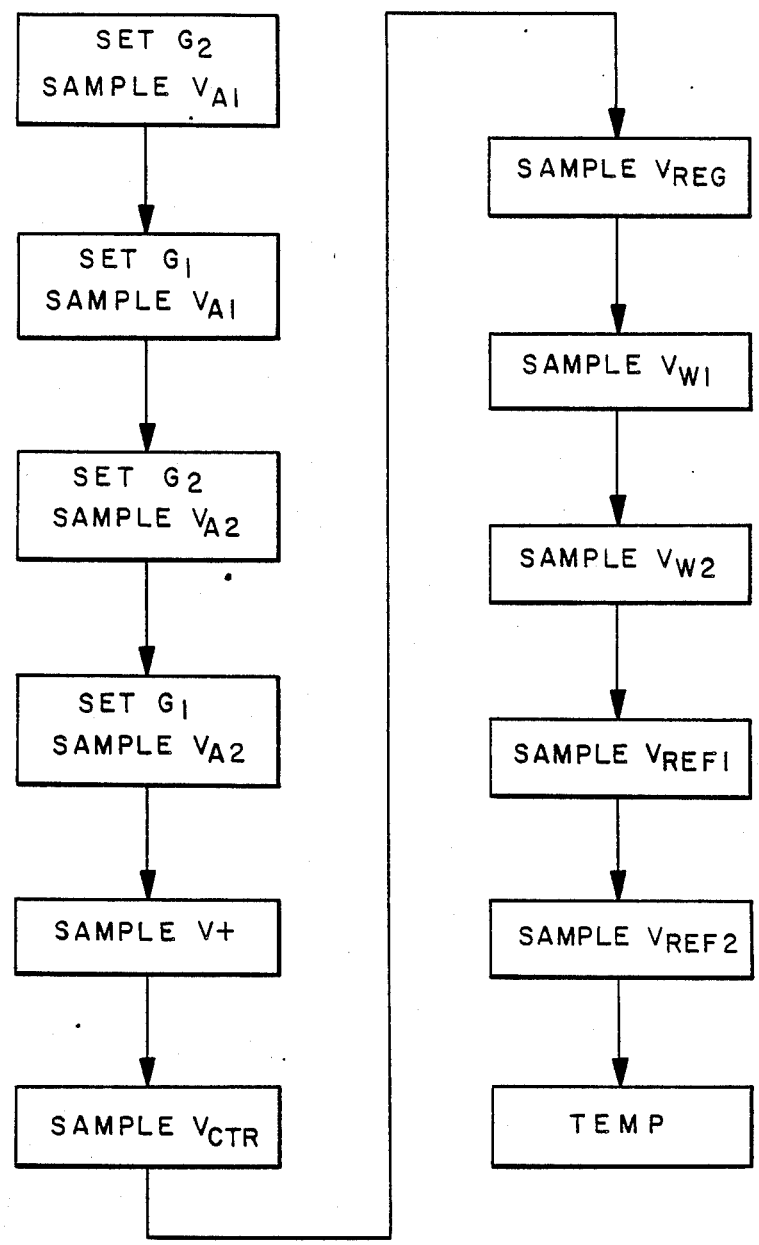
FIG. 8 is a flow diagram illustrating a sample sequence performed by the electronics of FIG. 6.

In operation, the timing and control unit 91 responds to the setting of the magnetic switch 101 to assume certain operational modes. Preferably, during one such mode, referred to as the standard operating mode, the TCU 91 will generate a gain select and multiplexer port select signal sequence in synchronism with a VCO and transmitter gating sequence to sample and transmit the voltage amplitude levels input to the multiplexer 89. One such sequence is illustrated in FIG. 8 where, during the period of one second, twelve discrete sampling periods are defined. These periods are illustrated in FIG. 8. Thus, in the first sampling period, the TCU 91 selects the high gain value ($G_2$) for the amplifiers 86 and 87. In the first period, the TCU 91 also provides a select signal that will connect the multiplexer input lead receiving the signal lead 106 to the output port of the multiplexer 89. This permits the sampling of the transformed, amplified voltage representing the current generated by the working electrode attached to the amplifier 86. At the same time, a signal turning on the VCO 96 and transmitter 98 is provided by the TCU 91; this signal is maintained throughout the sequence of FIG. 8. Conventionally, the amplitude of the signal ($V_{A1}$) on signal lead 106 will cause the VCO 96 to assume an oscillation frequency determined by the amplitude for so long as the signal lead is connected, through the multiplexer 89, to the output signal lead 114. In the second step of FIG. 7, the TCU 91 sets the lower gain value ($G_1$) for the amplifiers 86 and 87 and causes $V_{A1}$ to be sampled at this value. In succession, the high gain and low gain values for $V_{A2}$ on signal lead 110 are sampled. Next, the value of $V_+$, VCTR (the value of voltage on the counter electrode), and the output of the voltage regulator 94 are sampled. Sampling of the voltage regulator output permits the signal processing done by the VCO 96 and the transmitter 98 to be calibrated. In this regard, since a known value is expected for the product of the voltage regulator 94, the external electronics 84 can calibrate the telemetry received from the implanted electronics 82 by comparing, during sample period 7 of FIG. 8, the oscillation frequency of the modulating signal produced by the VCO 96 to the value expected for a voltage having the predetermined amplitude of $V_{reg}$. Next, the differential electrode voltage amplitudes and the reference amplitudes for the amplifiers 86 and 87, respectively, are sampled by action of the TCU 91. Finally, an indication of the internal temperature of the body within which the module of FIG. 1 is implanted is obtained by sampling the output of the temperature-controlled resistor 103.

Following the sample sequence of FIG. 8, the VCO 96 and XMT 98 are turned off for a period of time before another sampling sequence, identical with that of FIG. 7, is undertaken. In this manner, the lifetime of the battery 93 can be extended by reducing the total call on its resources by the oscillator and transmitter, 96 and 98, respectively.

The external unit 84 obtains and indicates the glucose and oxygen concentrations in the body by determining the values of the sensor currents produced by the working electrodes attached to the amplifiers 86 and 87. This is accomplished by receipt of the signal transmitted by the transmitter 98 through the skin barrier 80 and demodulation of the received signal by the receiver 122. The demodulated signal is fed to a processor 124, which can comprise a conventional microprocessor conventionally programmed to analyze and process the signals sampled by the internal electronics 82. In the preferred embodiment, the processor 124 is programmed to perform a five-step procedure for determining glucose and oxygen concentrations. In the procedure, the processor first calculates the bulk medium oxygen concentration from the current produced by the working electrode connected to the oxygen sensor. In this regard, the frequency of the demodulated oscillation is converted to the value of current amplitude produced by the oxygen sensor. This corresponds to processing the sample of $V_{A1}$. Second, the current expected from the glucose sensor at the calculated bulk medium oxygen concentration in the absence of glucose is determined utilizing a previously-determined linear calibration curve for the glucose sensor response to oxygen in the absence of glucose. In the third step, the value of the current actually produced by the glucose sensor is calculated, for example, from the value of $V_{A2}$, and is divided by the current calculated in step 2 from the linear calibration curve. In the fourth step, the ratio of glucose concentration to oxygen concentration in the bulk medium is determined from the value calculated in step 3 using a predetermined non-linear relationship between the glucose concentration ratio and the normalized current obtained in step 3. Finally, in step 5, the processor 124 multiplies the glucose concentration to oxygen concentration ratio of step 4 by the oxygen concentration calculated in step 1 to obtain the absolute value for the glucose concentration.

In the reduction to practice of the glucose sensing device of the invention, a dual lumen glucose monitoring catheter and an associated internal electronics module were implanted percutaneously into the fermoral vein of a dog. The animal was given an intravenous injection of glucose to demonstrate the sensor's performance. A conventional graphics plotter was used to plot various ones of the parameters sampled by the internal electronics 82. The samples were obtained by conventional programmed conversion of the results of the calculations described above. It will be evident to those skilled in the art that the program of the processor 124 can include such conversion means. The output plots show the recorded current of an oxygen reference electrode, reflecting the oxygen flux from the dog's venous blood. Another plot was made indicating the glucose electrode current, or the glucose-dependent oxygen current. In a third plot, the oxygen partial pressure of the venous blood was provided as determined by calibration of the first plot against an independent blood-gas oxygen measurement performed on the blood of the dog. Finally, a plot of the venous blood glucose concentration was obtained by substraction of the currents of the first and second plots after appropriate calibration. The plot was provided both in the form of a line plot of the current from the glucose electrode and a dot plot showing the glucose concentration as determined by an independent conventional method.

Obviously, many modifications and variations of this invention are possible in light of the above teachings, and, it is therefore understood that the invention may be practiced otherwise than as specifically described.

We claim:

1. An electrochemical system implantable into a body for detecting glucose and oxygen levels in fluids or tissues therein and capable of transmitting information about said glucose and oxygen levels outside said body, comprising:
   an elongate housing implantable in a body, said housing having a tip and being permeable to oxygen along its length;
   first and second oxygen sensor means for measuring an oxygen content differential in bodily fluids or tissues, said first and second oxygen sensor means disposed in tandem in said housing in a discontinous, spaced-apart relationship. said first and second oxygen sensor means recessed in said housing from said tip. said first oxygen sensor means being unaltered and said second oxygen sensor means contacting glucose oxidase for oxidation of glucose;
   implantable electronic circuit means responsive to said first and second oxygen sensor means for providing a signal indicative of an oxygen content differential in said fluids or tissues;
   telemetry means for communicating said signal from the interior to the exterior of said body; and
   an external processing means outside of said body and responsive to said telemetry means for converting said oxygen content differential to glucose level indications.

2. The electrochemical system of claim 1 wherein said first oxygen sensor means is behind said second oxygen sensor means and said housing comprises a hollow catheter made of oxygen permeable material drawn from the group consisting of polydimethylsiloxane, polymers of tetrafluoroethylene or its fluoro-chloro analogs alone or as copolymers with ethylene or propylene, polyethylene, polypropylene, cellulose acetate, and other oxygen-abiding polymeric materials.

3. The electrochemical system of claim 2 wherein said catheter is a multilumen catheter and said first oxygen sensor means is disposed in a first lumen of said catheter and said second oxygen sensor means is disposed in a second lumen of said catheter.

4. The electrochemical system of claim 2 wherein said first oxygen sensor means comprises at least three elongated electrodes and a support means for electrically insulating said three electrodes from one another and for supporting said three electrodes in a parallel, spaced-apart relationship.

5. The electrochemical system of claim 2 wherein said second oxygen sensor comprises at least three elongated electrodes and a support means for electrically insulating said three electrodes from one another and for supporting said three electrodes in a parallel, spaced-apart relationship,
   a hydrophobic membrane surrounding said three electrodes; and
   a second membrane positioned in said housing between said hydrophobic membrane and said tip, said second membrane contacting said hydrophobic membrane, containing glucose oxidase, and being accessible to bodily fluids or tissues through said tip.

6. The electrochemical system of claim 5 wherein said second membrane is permeable to glucose and oxygen, and is fabricated from hydrophilic materials drawn from the group consisting of polyacrylamide, cross-linked proteins, polyhydroxy-ethylmethacrylate and its derivatives, and other hydrophilic proteins, polymers and copolymers, thereof.

7. The electrochemical system of claim 5 wherein said hydrophobic membrance is permeable to oxygen and relatively impermeable to glucose, and is fabricated from polydimethylsiloxyane, polymers of tetrafluoroethylene, or its fluoro chloro analogs or as copolymers with ethylene or propylene, polyethylene, polypropylene, cellulose acetate, and other oxygen-abiding polymeric materials.

8. The electrochemical system of claims 4 or 5 wherein said three electrodes include a working electrode, a counter electrode, and a reference electrode.

9. The electrochemical system of claim 1 wherein said housing includes a bilumen catheter.

10. The electrochemical system of claim 9 wherein said first and second oxygen sensor means are situated in respective lumens of said bilumen catheter.

11. The electrochemical system of claim 1 wherein said first and second oxygen sensor means are for producing respective first and second sensor signals, each of said sensor signal representative of an oxygen level and said electronic circuit means includes means for intermittently sampling said first and second sensor signals to produce said differential signal.

12. The electrochemical system of claim 10 wherein said telemetry means includes a voltage-controlled oscillator having a frequency of oscillation determined by a sensor signal and a transmitter which modulates a transmitter carrier in response to the frequency of oscillation of said voltage-controlled oscillator.

13. The electrochemical system of claim 11 wherein said external processing means includes demodulating means for obtaining said first and second sensor signals from said transmitted carrier and programmable processing means for combining said first and second sensor signals according to predetermined calibration characteristics to obtain said glucose levels.

14. An implantable electrochemical sensor, comprising:
   an elongate housing, permeable to oxygen along its length, having a tip, and implantable in human tissue; and
   first and second oxygen sensor means for measuring an oxygen content differential in bodily fluids or tissues, said first and second oxygen sensor means disposed in tandem in said housing in a discontinuous, spaced-apart relationship, said first and second oxygen sensor means recessed in said housing from said tip, said first oxygen sensor means being unaltered and said second oxygen sensor means contacting glucose oxidase for oxidation of glucose.

15. The implantable electrochemical sensor of claim 14 wherein said first oxygen sensor means is behind said second oxygen sensor means and said housing comprises a hollow catheter made of oxygen permeable material drawn from the group consisting of polydimethylsiloxane, polymers of tetrafluoroethylene or its fluoro-chloro analogs alone or as copolymers with ethylene or propylene, polyethylene, polypropylene, cellulose acetate, and other oxygen-abiding polymeric materials.

16. The implantable electrochemical sensor of claim 15 wherein said catheter is a multilumen catheter and said first oxygen sensor means is disposed in a first lumen of said catheter and said second oxygen sensor means is disposed in a second lumen of said catheter.

17. The implantable electrochemical sensor of claim 15 wherein said first oxygen sensor means comprises at least three elongated electrodes and a support means for electrically insulating said three electrodes from one another and for supporting said three electrodes in a parallel, spaced-apart relationship.

18. The implantable electrochemical sensor of claim 15 wherein said second oxygen sensor comprises at least three elongated electrodes and a support means for electrically insulating said three electrodes from one another and for supporting said three electrodes in a parallel, spaced-apart relationship;

a hydrophobic membrane surrounding said three electrodes; and
a second membrane, positioned in said housing between said hydrophobic membrane and said tip, said second membrane contacting said hydrophobic membrane, containing glucose oxidase, and being accessible to bodily fluids or tissues through said tip.

19. The implantable electrochemical sensor of claim 18 wherein said second membrane is permeable to glucose and oxygen, and is fabricated from hydrophilic materials drawn from the group consisting of polyacrylamide, cross-linked proteins, polyhydroxy-ethylmethacrylate and its derivatives, and other hydrophilic proteins, polymers and copolymers, thereof.

20. The implantable electrochemical sensor of claim 18 said hydrophobic membrane is permeable to oxygen and relatively impermeable to glucose, and is fabricated from polydimethylsiloxyane, polymers of tetrafluoroethylene, or its fluoro chloro analogs or as copolymers with ethylene or propylene, polyethylene, polypropylene, cellulose acetate, and other oxygen-abiding polymeric materials.

21. The implantable electrochemical sensor of claim 17 or 18 wherein said three electrodes include a working electrode, a counter electrode, and a reference electrode.

22. The implantable electrochemical sensor of claim 14 wherein said housing includes a bilumen catheter.

23. The implantable electrochemical sensor of claim 22 wherein said first and second oxygen sensor means are situated in respective lumens of said bilumen catheter.

* * * * *